US010753929B2

(12) United States Patent
Choi et al.

(10) Patent No.: US 10,753,929 B2
(45) Date of Patent: Aug. 25, 2020

(54) PORTABLE URINE ANALYSIS DEVICE

(71) Applicant: PROTEC LIFE & HEALTH Co., Ltd., Gyeonggi-do (KR)

(72) Inventors: Sung Hwan Choi, Gyeonggi-do (KR); In Soo Jeon, Seoul (KR); Kyu Jeong Han, Gyeonggi-do (KR)

(73) Assignee: PROTEC LIFE & HEALTH Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/299,115

(22) Filed: Mar. 11, 2019

(65) Prior Publication Data
US 2019/0204315 A1     Jul. 4, 2019

Related U.S. Application Data

(63) Continuation of application No. PCT/KR2016/010348, filed on Sep. 13, 2016.

(30) Foreign Application Priority Data

Sep. 12, 2016  (KR) .................. 10-2016-0117406

(51) Int. Cl.
*G01N 33/543*      (2006.01)
*B01L 3/00*        (2006.01)
(Continued)

(52) U.S. Cl.
CPC .......... *G01N 33/54386* (2013.01); *B01L 3/52* (2013.01); *G01N 33/487* (2013.01);
(Continued)

(58) Field of Classification Search
CPC ............ G01N 33/54386; G01N 33/50; G01N 33/497; G01N 33/487; G01N 35/00;
(Continued)

(56) References Cited

U.S. PATENT DOCUMENTS 3,918,910 A * 11/1975 Soya .................. G01N 21/8483
                                                              422/66
4,961,431 A * 10/1990 Ikenaga ............. A61B 5/14507
                                                             600/573
(Continued)

FOREIGN PATENT DOCUMENTS

KR      20090002942       *  1/2009  .......... G01N 33/493
KR    1020090002942          1/2009
(Continued)

*Primary Examiner* — Benjamin R Whatley
*Assistant Examiner* — Curtis A Thompson
(74) *Attorney, Agent, or Firm* — JCIP Global Inc.

(57) ABSTRACT

Provided is a portable urine analysis device including: a main housing including: a tray including a tray driving unit in which a strip is loaded to introduce and withdraw the strip, wherein the strip that is completely analyzed is dropped via the tray, and a urine analysis module analyzing urine of the strip to generate urine analysis information; a sub-housing coupled under the main housing and including an accommodation box which is slidable while the accommodation box has a space that temporarily stores the dropped strip; and a support supporting the sub-housing. According to the portable urine analysis device, urine is analyzed by using the strip as a medium, portability is reinforced with a compact and slim structure, and a completely analyzed strip is disposed of hygienically.

9 Claims, 6 Drawing Sheets

(51) Int. Cl.
  *G01N 33/487* (2006.01)
  *G06Q 50/22* (2018.01)
  *G01N 33/497* (2006.01)
  *G01N 33/50* (2006.01)
  *A47K 17/02* (2006.01)
  *G01N 21/78* (2006.01)
  *G01N 21/00* (2006.01)
  *G01N 21/27* (2006.01)
  *G01N 1/36* (2006.01)
  *G01N 33/52* (2006.01)
  *G01N 35/00* (2006.01)
  *G01N 33/493* (2006.01)

(52) U.S. Cl.
  CPC ........... *G01N 33/497* (2013.01); *G01N 33/50* (2013.01); *G06Q 50/22* (2013.01); *A47K 17/02* (2013.01); *B01L 2200/16* (2013.01); *B01L 2300/0825* (2013.01); *G01N 1/36* (2013.01); *G01N 21/00* (2013.01); *G01N 21/27* (2013.01); *G01N 21/78* (2013.01); *G01N 33/493* (2013.01); *G01N 33/52* (2013.01); *G01N 35/00* (2013.01)

(58) Field of Classification Search
  CPC .......... G01N 33/52; G01N 1/36; G01N 21/27; G01N 21/00; G01N 21/78; G01N 33/493; G01N 33/48792; G06Q 50/22; B01L 3/52; B01L 2300/0825; B01L 2200/16; A47K 17/02; A61L 35/207; A61L 10/007; A61L 5/20
  See application file for complete search history.

(56) References Cited

U.S. PATENT DOCUMENTS

| | | | |
|---|---|---|---|
| 2007/0264157 A1* | 11/2007 | Takagi | G01N 21/8483 422/64 |
| 2010/0228148 A1* | 9/2010 | Kim | A61B 5/412 600/573 |
| 2010/0267049 A1* | 10/2010 | Rutter | G01N 21/6428 435/7.1 |
| 2017/0284925 A1* | 10/2017 | Spangenberg | A61B 10/007 |

FOREIGN PATENT DOCUMENTS

| | | | | |
|---|---|---|---|---|
| KR | 101080832 | | 11/2011 | |
| KR | 101095280 | | 12/2011 | |
| KR | 20120062177 | * | 6/2012 | ............ G01N 33/52 |
| KR | 101257299 | | 4/2013 | |

* cited by examiner

PORTABLE URINE ANALYSIS DEVICE

CROSS-REFERENCE TO RELATED APPLICATION

This application is a Continuation of PCT International Application No. PCT/KR2016/010348 filed on Sep. 13, 2016, which claims the priority of Korean Patent Application No. 10-2016-0117406, filed on Sep. 12, 2016. The entirety of the above-mentioned patent applications is hereby incorporated by reference herein and made a part of this specification.

BACKGROUND OF THE DISCLOSURE

Field of the Disclosure

The present disclosure relates to a portable urine analysis device, and more particularly, to a urine analysis device in a shape of an integral unit of a portable size, wherein a strip smeared with urine is analyzed to determine a health condition of a user regarding an analysis result in real time, and at the same time, the urine analysis device is linked with a separate electronic device and is not only operated but may also store/control urine analysis information of each user, and which allows to conveniently dispose of the strip after completing the analysis.

Description of Related Art

Healthcare refers to a total health care business integrating medical treatment services and disease prevention and control, and while management of health is one of the major issues, it is particularly important to regularly check health conditions.

Blood tests are one way that is widely used to check one's health condition, but they involve a cumbersome method to analyze blood by using complicated processes such as a blood collecting process and centrifugation, and thus has limitations and an inconvenience that it can only be properly conducted in specialized institutions such as hospitals. There are also still many obstacles to conduct a remote blood test.

On the other hand, a urine test is convenient in that the test can be conducted simply by visual inspection of physical properties such as the color or turbidity of urine, with unaided eyes.

As a next advanced step of the urine test based on physical properties, a chemical test for conducting a semi-qualitative analysis by smearing urine on a strip is available, and in particular, by the commercialization of an analyzer performing optical analysis of strips, the analyzer is attached to a urinal or is manufactured as a portable analyzer.

KR 10-1080832(B) discloses an analyzing device mounted on a toilet seat, whereby a strip is placed along a dropping line which urine drops during user's urination to smear the urine on the strip to analyze. However, the analyzing device has a complicated structure and is thus expensive, and it is difficult to commercialize the same to replace blood tests.

On the other hand, KR 10-1095280(B) and KR 10-1257299(B) disclose a portable urine analyzer that ensures portability, simplicity, and professional analysis by using a strip as a medium, and also provides precise urine test results.

However, the portable urine analyzer described above does not provide any proper means to recollect or dispose of strips that are completely analyzed, and thus, it is burdensome to dispose of the completely analyzed strips, or there is the inconvenience that the user's hands become dirty.

Thus, there is a need for development of a novel and inventive portable urine analysis device that is easy to carry and also allows disposal of analyzed strips more conveniently and hygienically.

SUMMARY OF THE DISCLOSURE

Provided is a portable urine analysis device which is easy to carry and operate and whereby analyzed strips may be easily disposed of.

Also provided is a portable urine analysis device in which a strip is loaded in a strip loading portion of a slidable tray, wherein the strip loading portion has a openable structure and completely analyzed strips are dropped via an opening operation of the strip loading portion and conveniently and temporarily stored in an accommodation box under the strip loading portion.

Also provided is a portable urine analysis device in which transfer of a tray and an operation of dropping analyzed strips are closely linked with each other to seek reduction in battery power consumption.

Also provided is a portable urine analysis device which is remotely controlled in conjunction with an application installed on a table PC, a mobile device, and which also manages urine analysis information of each user.

Also provided is a portable urine analysis device which provides means to conveniently load a sheet in an accommodation box to ensure the hygiene of the space where strips are stored.

According to an aspect of the present disclosure, there is provided a portable urine analysis device including: a main housing comprising a tray comprising a strip loading portion loading a strip and a tray driving unit withdrawing the strip to the outside and introducing the strip into a urine analysis area, wherein the strip loading portion is opened to drop the strip that is completely analyzed, and a urine analysis module analyzing urine of the strip at a side of the urine analysis area to generate urine analysis information; a sub-housing coupled under the main housing and comprising an accommodation box which is slidable while the accommodation box has a space that temporarily stores the dropped strip; and a support supporting the sub-housing.

In addition, at least one of the main housing and the sub-housing may include at least one LED module and color sensor module emitting light toward the support.

In addition, the strip loading portion may include a front loading portion facing the front and a rear loading portion that is openably connected to the front loading portion, and the tray may include an opening controller comprising a push frame extending from a side of the rear loading portion toward the front loading portion and an a push spring mounted to the push frame to provide an elastic moving force of the push frame.

According to a portable urine analysis device of the present disclosure, 1) the portable urine analysis device is easy to carry and provides a convenient analysis method by using a strip, and also, completely analyzed strips may be disposed of hygienically, and 2) a compact structure may be maintained, and the analyzed strips may be dropped and temporarily stored in an accommodation box to thereby reduce the costs and increase the convenience during use, and 3) a basis for reducing power may be provided by dropping analyzed strips by using a movable structure of a tray, and 4) the portable urine analysis device may be linked with an external electronic device to be remotely controlled and also provide various health guide information such as diet therapy (diet menus), kinesiotherapy, and other therapies customized for each user based on each user's urine analysis information, and also to provide a function of searching for nearby hospitals in case of a health problem and making a reservation, and also, 5) a sheet that hygienically covers the accommodation box temporarily storing the strips, may be provided in a semi-automatic/automatic manner to reinforce the hygiene and also prevent bad odor.

DESCRIPTION OF THE EMBODIMENTS

Figure 1:
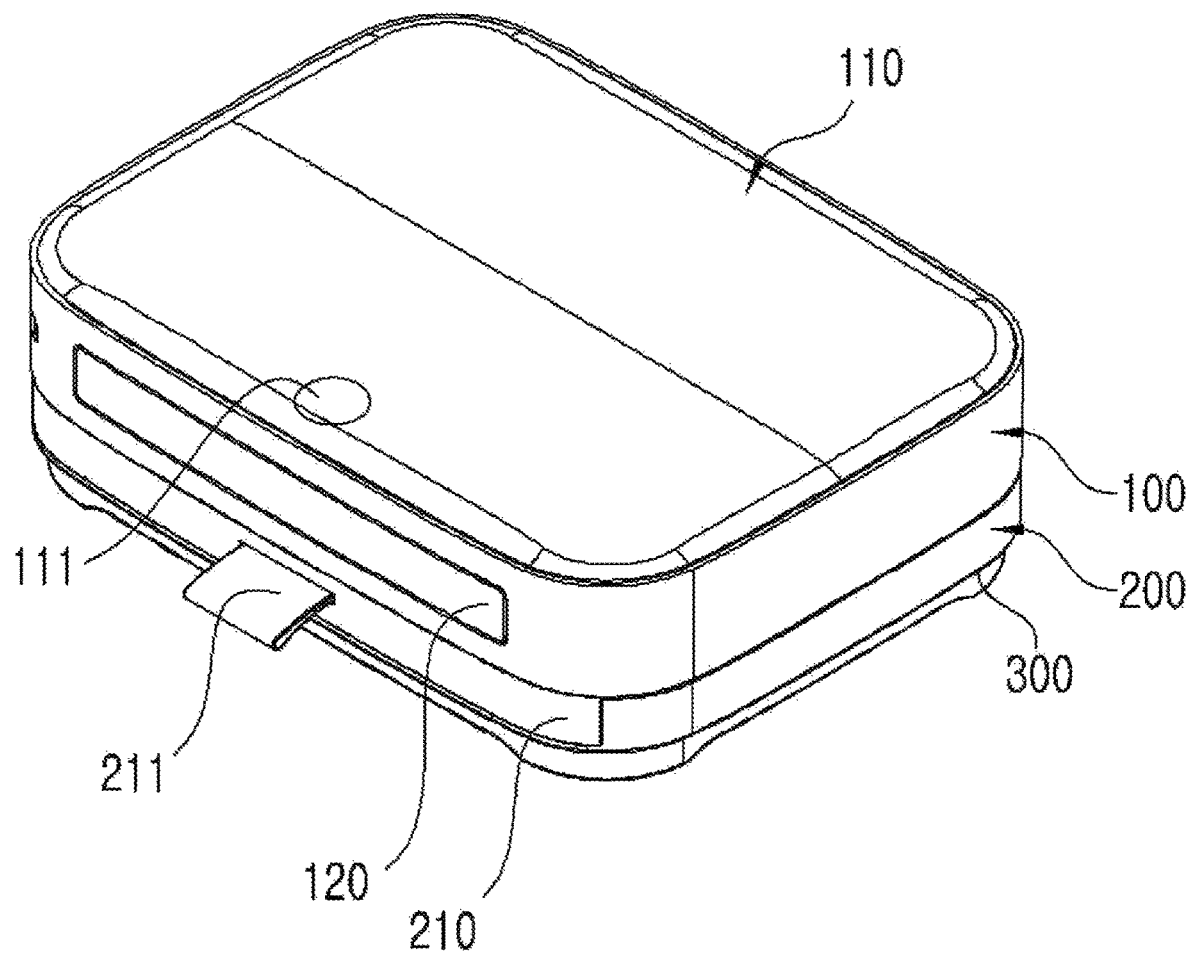
FIG. 1 is a perspective view of an overall outer appearance of an analysis device according to the present disclosure.

A portable urine analysis device includes: a main housing including a tray including a strip loading portion loading a strip and a tray driving unit withdrawing the strip to the outside and introducing the strip into a urine analysis area, wherein the strip loading portion is opened to drop the strip that is completely analyzed, and a urine analysis module analyzing urine of the strip at a side of the urine analysis area to generate urine analysis information; a sub-housing coupled under the main housing and including an accommodation box which is slidable while the accommodation box has a space that temporarily stores the dropped strip; a support supporting the sub-housing.

Hereinafter, the present disclosure will be described more fully with reference to the accompanying drawings, in which exemplary embodiments of the present disclosure are shown. The attached drawings are not illustrated based on the scale, and like reference numerals denote like elements in the drawings.

FIG. 1 is a perspective view of an overall outer appearance of an analysis device according to the present disclosure.

Instead of a structure to be attached to a urinal to collect urine, a urine analysis device according to the present disclosure is a modular integral unit type and thus may be arranged anywhere in various places, thereby providing convenience, In addition, the urine analysis device according to the present disclosure also has a compact size that increases portability, and as illustrated in FIG. 1, the urine analysis device according to the present disclosure consists of a combined structure including a main housing 100 and a sub-housing 200 that is integrally coupled under the main housing 100.

In brief, the main housing 100 according to the present disclosure is characterized by including a tray 120 and a urine analysis module 140, wherein the main housing 100 has a rectangular parallelepiped shape or a three-dimensional shape corresponding to the rectangular parallelepiped with an upper surface thereof integrally covered by a cover 110.

In addition, the sub-housing 200 according to the present disclosure is characterized by including an accommodation box 210 that temporarily stores a strip 10 dropped from the tray 120 after urine analysis is completed.

In addition, the urine analysis device of the present disclosure may be linked with an external electronic device to record/store/manipulation/control urine analysis information, and to this end, the urine analysis device may include a controller 400 having a communication function, and the controller 400 may be provided in one of the main housing 100 and the sub-housing 200, wherein it is preferable that the controller 400 is provided in the main housing 100 that generates urine analysis information by using the urine analysis module 140.

In addition, a support 300 is mounted on a lower surface of the sub-housing 200 to stably support the main housing 100 and the sub-housing 200 and at the same time, as will be described later, provides a structural basis to provide health condition information as differentiated visual representations by illumination.

Hereinafter, the urine analysis device according to the present disclosure will be described in detail with reference to FIG. 2.

Figure 2:
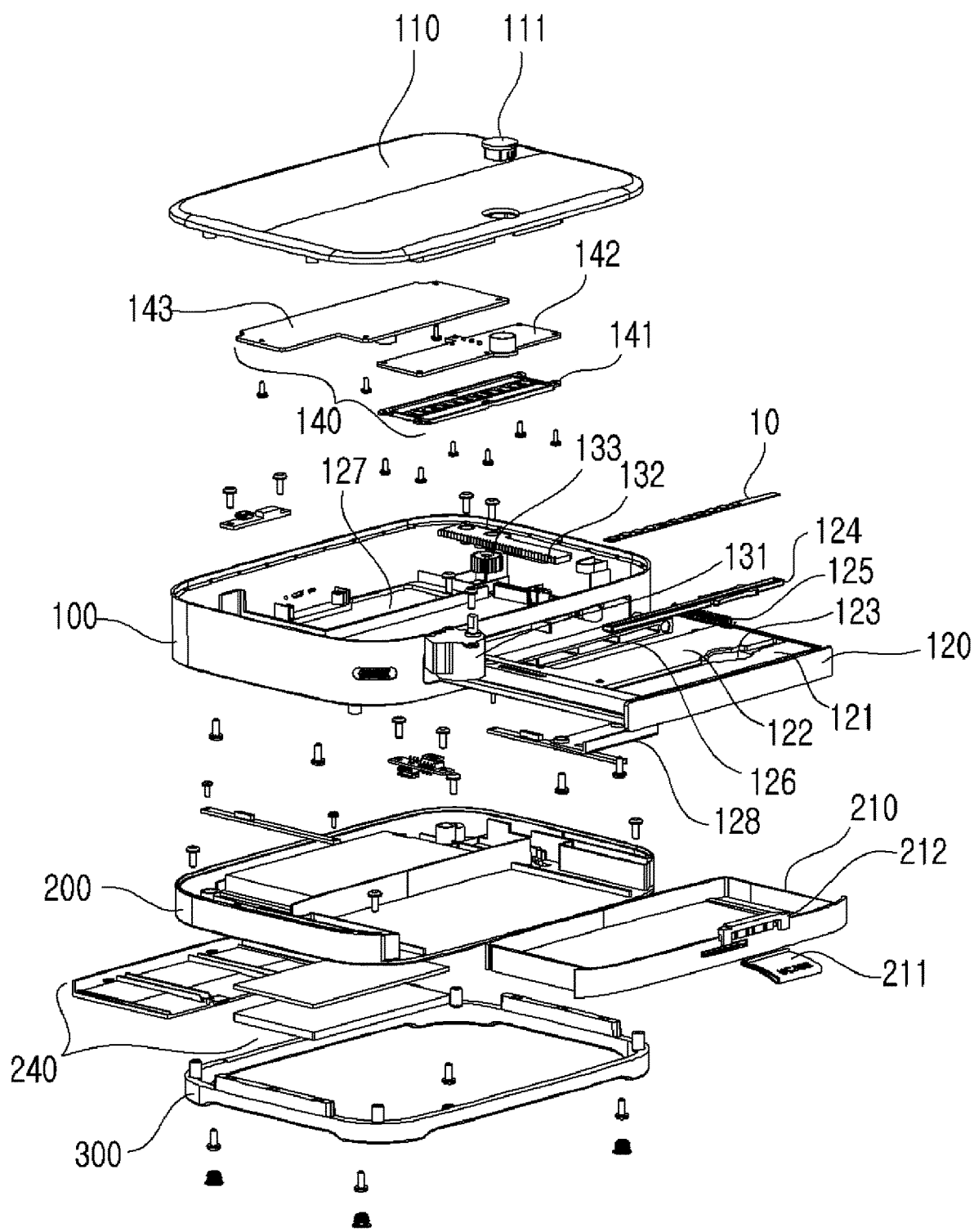
FIG. 2 is a disassembled perspective view of an analysis device according to the present disclosure.

FIG. 2 is a disassembled perspective view of an analysis device according to the present disclosure.

As described above, the analysis device according to the present disclosure has a vertical stack structure in which the main housing 100 and the sub-housing 200 are integrally coupled, and elements and functions thereof from the cover 110 in an upper portion to the support 300 in a lower portion will be described in detail.

A switch 111 is mounted at a side of the cover 110 covering an upper surface of the main housing 100, and a main function of the switch 111 is to generate an ON/OFF signal, and also, the switch 111 has a function of generating an additional signal such as LED lighting control, external device connection control or the like, and to this end, the switch 111 may be formed of not just one switch, but of a group of a plurality of switches to generate respective additional signals or may be a touch screen-based switch.

In addition, referring back to FIG. 1, at least one indication lamp (three in the drawing) is mounted around the switch 111, and the indication lamp may perform a function of differentially displaying a health condition based on an ON/OFF state, indication of a remaining amount of battery, an operational state, and urine analysis information. In particular, to differentially display a health condition of a user via an indication lamp, it is preferable that at least two or more indication lamps are provided.

The urine analysis module 140 is mounted in an upper space of the main housing 100 which is at a lower surface of the cover 110, and the urine analysis module 140 is mounted on one of the lower surface of the cover 110 or on an upper portion of the main housing 100, and is thus located above a urine analysis area.

The urine analysis module 140 according to the present disclosure performs a function of checking a health condition of a user by analyzing urine components of the strip 10, and in general, an interface for urine analysis is based on, for example, tests of physical properties such as the color/turbidity of urine, semi-qualitative chemical detection performed using a strip, component analysis using a microscope, or the like, and the urine analysis module 140 is not limited to any one of these, but since the interface based on optical detection using the strip 10 ensures both convenience and accuracy at the same time, description herein will focus on the optical detection-based interface.

The urine analysis module 140 according to the present disclosure based on an optical detection interface consists of a photo-sensor 142 and a PBA-based analysis control unit 143, and the photo-sensor 142 detects a color of each sector of the strip 10 smeared with urine, and the analysis control unit 143 analyzes the color to generate urine analysis information by a user.

In addition, the analysis control unit 143 may be linked with a communication module 410, which will be described later, or include a communicator and transmit the urine analysis information to an external electronic device such as a table PC to record/store each user's urine analysis information.

In addition, an additional LED module 141 may be mounted in the urine analysis module 140, and in the present disclosure, the LED module 141 may include at least one LED in one of the main housing 100 and the sub-housing 200, and the main housing 100/the sub-housing 200 may be formed of a semi-transparent material so that a LED light may be identified from the outside, and the LED module 141 provides a function of visually displaying a urine analysis process or a completed state of urine analysis via flickering of the LED module 141, and may also provide a function of indirect illumination by emitting light toward the support 300. In addition, the LED module 141 may include a package including a color sensor, that is, a color sensor module, and thus may also perform a function of performing color analysis of the strip 10 after optical analysis of urine.

Figure 3:
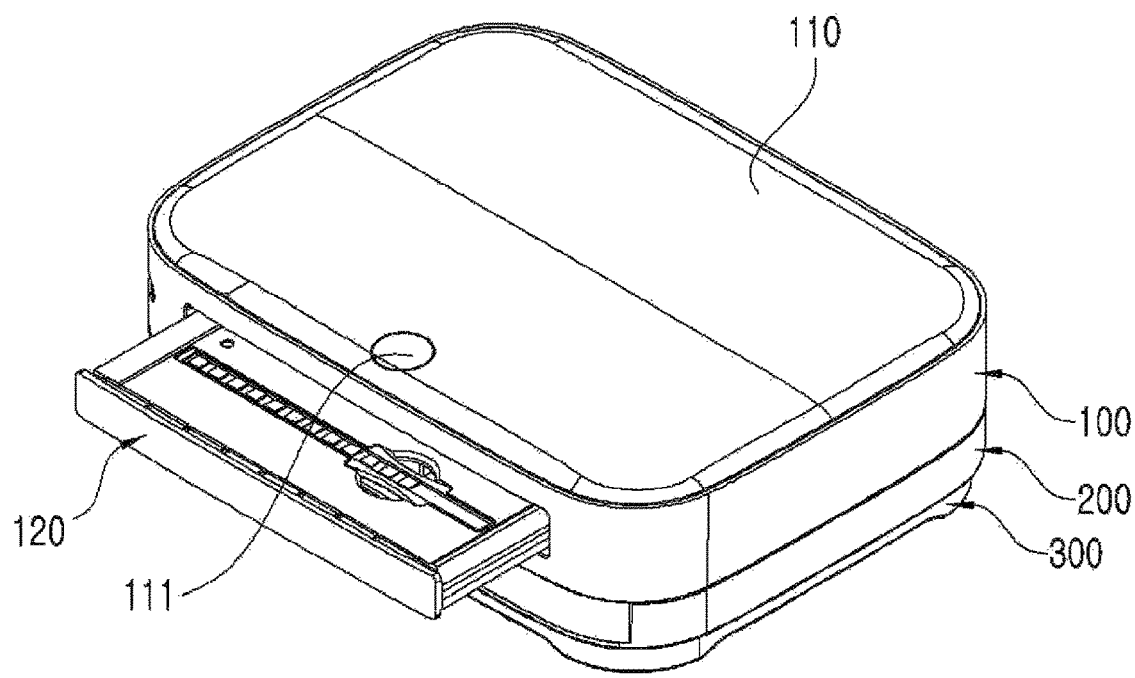
FIG. 3 is a conceptual diagram of a state in which a strip is loaded in a tray, according to the present disclosure.

FIG. 3 is a conceptual diagram of a state in which a strip is loaded in a tray, according to the present disclosure.

The tray 120 according to the present disclosure is withdrawn out of the main housing 100 such that a user may load the strip 10 in the tray 120, and also, the strip 10 is introduced using the tray 120 into the main housing 100 to a urine analysis area so that the urine analysis module 140 analyzes urine smeared on the strip 10, and moreover, the tray 120 performs a function of dropping the strip 10 downwards after completing urine analysis.

In detail, the tray 120 is horizontally withdrawn out of/introduced into the main housing 100 via a tray driving unit 130.

A mechanical structure for introducing/withdrawing a tray may be various, and FIG. 2 illustrates an example in which the tray driving unit 130 includes a rack 132 that is supported on an internal surface of the main housing 100 and is coupled to an external surface of the tray 120 and a pinion 133 that is linked with the rack 132 and rotated forward/backward by driving of a motor 131 to introduce/withdraw the tray 120 to which the rack 132 is coupled. Here, in order to prevent the tray 120 from being unnecessarily additionally withdrawn to the front side of the analysis device, a stopper 128 may be mounted on a side of the tray driving unit 130 or the tray 120.

According to this configuration, when the switch 111 is operated via user's manipulation or wireless control by an external electronic device, the tray 120 is withdrawn out of the main housing 100 by a certain length via forward rotation of the motor 131 so that the user loads the strip 10 smeared with urine in a strip loading portion which can be regarded as a support surface of the strip 10, and after a certain interval, the user may introduce the tray 120 into the main housing 100 via reverse rotation of the motor 131 such that the strip 10 loaded in the tray 120 is moved up to the urine analysis area which is a position under the urine analysis module 140 to perform urine analysis.

In addition, in order to drop the strip 10 downwards after completing the analysis, the tray 120 includes a strip loading portion that is configured openably. That is, the strip loading portion may include a front loading portion 121 that is located in an exterior with respect to a hollow portion 123 in which the strip 10 is loaded, and a rear loading portion 122 that is adjacent to the front loading portion 121 and takes up a rear side, and one of the front loading portion 121 and the rear loading portion 122 may be opened by control of an opening controller.

Here, a strip bar 124 is loaded over the hollow portion 123 and the strip 10 is located thereon to thereby allow the photo-sensor 142 to efficiently perform optical analysis while minimizing reflectivity.

A structure in which the front loading portion 121 and the rear loading portion 122 are openable via an opening controller may be formed of various mechanical components.

As an example of the opening controller, the opening controller may be formed of a combination of rack/pinion that are driven by motive power of a motor while they are connected to one of the front/rear loading portions 121 and 122 or a slidable structure moving along a guide rail. That is, when analysis of the strip 10 is completed, at least one of the front/rear loading portions 121 and 122 is opened, via a driving control of the opening controller, to drop the strip 10 that is completely analyzed and store the strip 10 in the accommodation box 210 located therebelow.

However, according to the present disclosure, a specific structure may be provided, in which just the motor 131 in the tray driving unit 130 described above is used to also drive the opening controller to open one of the front/rear loading portions 121 and 122 to thereby save battery power consumption and also provide an effect of visually presenting completion of the analysis to a user, which will be described with reference to FIGS. 2 and 4.

Figure 4:
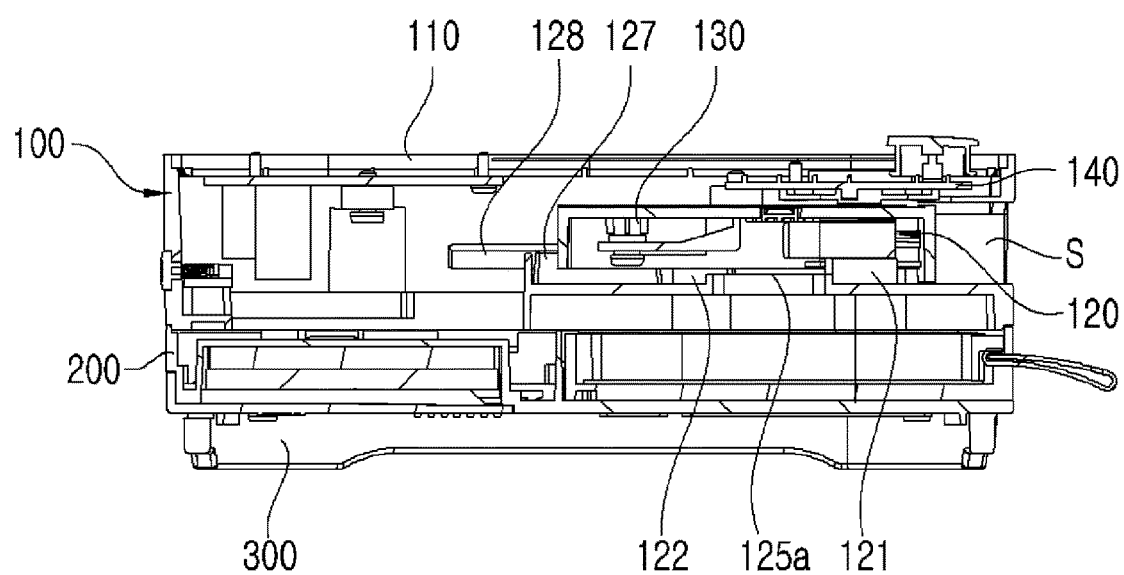
FIG. 4 is a conceptual diagram illustrating a state in which a tray according to the present disclosure is moved backwards to a urine analysis area.

FIG. 4 is a conceptual diagram illustrating a state in which a tray according to the present disclosure is moved backwards to the urine analysis area.

In the main housing 100, the tray 120 is withdrawn to the outside to be introduced into an internal space where the urine analysis area is located, and here, there may be a remaining space at a back of the urine analysis area, and when the urine analysis is completed, the tray 120 is further introduced via reverse rotation of the motor 131 (rotation in a introducing direction) into an interior of the main housing 100, that is, to the remaining space, and thus space S where the tray 120 is further introduced into the remaining space of the main housing 100 is formed when viewed from the front side of the analysis device.

Here, a loading space of the tray 120 is also broader than the front/rear loading portion, and thus, a space where the front loading portion 121 may be moved over a certain width may be ensured.

As shown in FIGS. 2 and 4, the opening controller according to the present disclosure may include a push frame 125a extending from a lateral surface of the rear loading portion 122 toward the front loading portion 121 by a certain length and a push spring 125 mounted to provide an elastic force to the push frame 125a.

That is, when urine analysis is completed, the tray 120 is further introduced into the remaining space at a back of the main housing 100 via reverse rotation of the motor 131, and in this process, the rear loading portion 122 contacts an internal surface of the back of the main housing 100 to compress the push spring 125. The push spring 125 that is compressed is restored via an elastic force, and as the push spring 125 is restored, the front loading portion 121 is pushed to the front side of the analysis device, and according to this push, the front/rear loading portion 121 and 122 are spaced apart to thereby drop the strip 10 loaded on upper surfaces thereof.

Furthermore, in order to minimize impact to ensure durability when the rear loading portion 122 contacts the internal surface of the back of the main housing 100, a base 127 may be additionally mounted on the internal surface of the back of the main housing 100, and in accordance with this, a push bar 126 including a plurality of elastic protrusions may be mounted on a rear side surface of the rear loading portion 122 (that is, a surface contacting the base).

Accordingly, when the rear loading portion 122 contacts the internal surface of the back of the main housing 100, the elastic protrusions of the push bar 126 are compressed by a certain length to minimize impact and generate a repulsive force accordingly, thereby further providing a function that the push spring 125 is restored so as to push the front loading portion 121 to the front side of the analysis device more elastically.

According to the structure of the opening controller as described above, power may be saved, resistance to impact may be ensured, and also, opening of the front/rear loading portion may be ensured.

Figure 5:
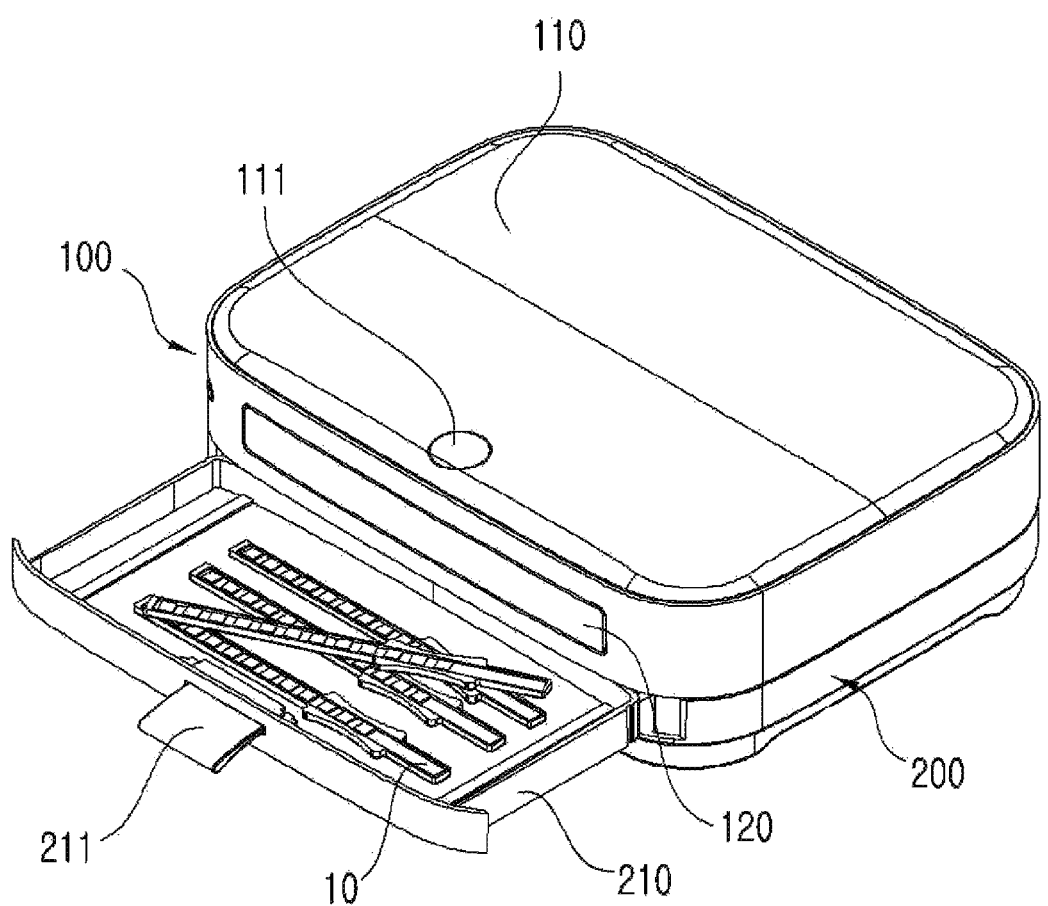
FIG. 5 is a conceptual diagram illustrating a state in which an analyzed strip is stored in an accommodation box according to the present disclosure.

FIG. 5 is a conceptual diagram illustrating a state in which a completely analyzed strip is stored in an accommodation box according to the present disclosure.

The sub-housing 200 according to the present disclosure includes an accommodation box 210.

The accommodation box 210 according to the present disclosure provides space for temporarily storing the strip 10 that is completely analyzed, as described above, and is slidable in a manner of a drawer to thereby enable a user to discard or scrap the strip 10 that is collected by a user and stored therein. A grip portion 211 functioning as a handle is formed on a front surface of the accommodation box 210 to allow a user to easily hold the same, and a locking bracket 212 may also be formed at a side of the accommodation box 210 to prevent unnecessary separation.

In addition, the sub-housing 200 may include a battery unit 240 in a peripheral space of the accommodation box 210, and the battery unit 240 may be an external power connecting type and also a rechargeable type, thus ensuring portability.

The support 300 that is integrally coupled to a lower side of the sub-housing 200 is in direct contact with a bottom surface, and as the support 300 includes legs to ensure aesthetic design features, and the analysis device according to the present disclosure is spaced apart from the bottom by a certain distance to ensure a stably supported state.

Figure 6:
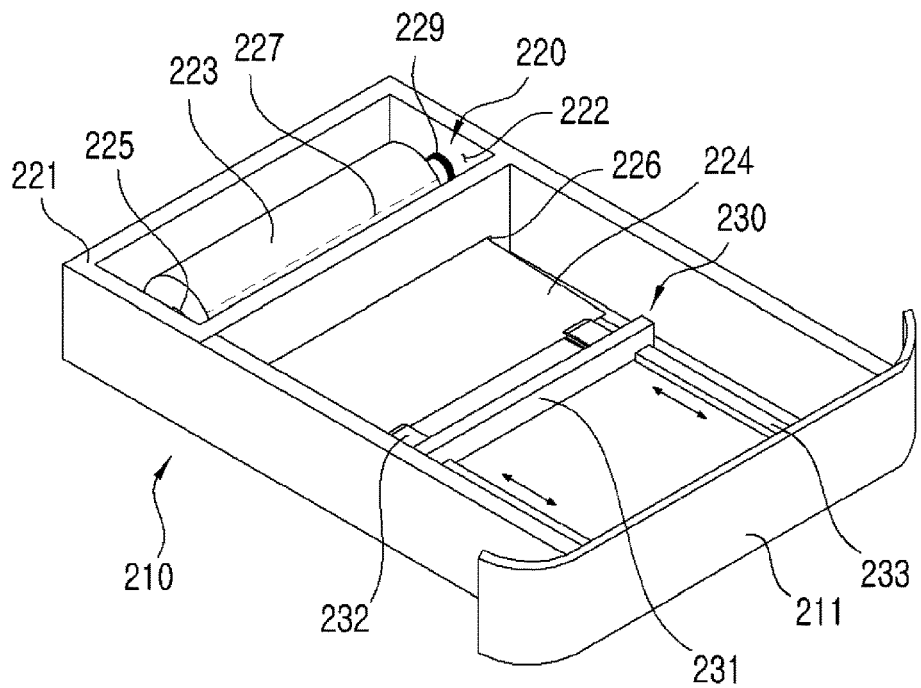
FIG. 6 is a perspective view of a modified embodiment of the accommodation box according to the present disclosure.

FIG. 6 is a perspective view of a modified embodiment of the accommodation box according to the present disclosure.

According to the above-described structure, the strip 10 which is completely analyzed may be hygienically stored in the accommodation box 210. However, since urine is still on the strip 10, even when dried, there is a possibility that an inner surface of the accommodation box 210 is contaminated or bad odor is caused unintentionally.

To solve this problem, a sheet providing unit 220 may be further provided at a back side of the accommodation box 210, in detail, on a rear internal surface thereof.

The sheet providing unit 220 provides a function of rewinding a roller 223, on which a sheet 224 is wound, in a space 222 formed in a sheet housing 221 to withdraw the sheet 224 through a slit 226 to cover a bottom surface of the accommodation box 210 and allow the strip 10 to be loaded on an upper surface of the sheet 224, thereby hygienically disposing of the strip 10. Here, the sheet 224 may be formed of a degradable vinyl material to surround the completely analyzed strip 10 eco-friendly and hygienically and thus to dispose of the same by discarding or the like. In addition, the sheet may also include an aromatic component to thereby prevent leakage of bad odor due to urine.

In detail, the sheet providing unit 220 includes the roller 223 that is rotatably fixed via a roller shaft 225 at a side of the space 222, and although not illustrated in the drawing, the corresponding space 222 may be opened or closed by a cover. The roller 223 is winding the sheet 224, and when the sheet 224 of the roller 223 is used up, the sheet 224 may be easily additionally inserted by opening the cover 110 or through an open upper surface of the sheet housing 221.

In addition, the slit 226 is formed at a side of the sheet housing 221, specifically, in a lower portion of a surface thereof which is facing the front of the accommodation box and is close to the bottom, and pull an end portion of the sheet 224, or by rotating the roller 223 in a rewinding direction, the sheet 224 may be withdrawn from the roller 223 to the outside of the slit 226 to thereby cover the bottom surface of the accommodation box 210.

In addition, by using a perforated line 227 formed in the sheet 224 as a broken line at certain intervals by depressing, wherein the sheet is preferably formed of a vinyl material, the user may use the sheet 224 by separating the same, or a saw blade (not shown) may be formed around a side portion of the slit 226 to cut the sheet 224.

By using the sheet providing unit 220, the user's hand does not have to touch urine smeared on the strip 10, and moreover, the strip 10 may also be disposed of hygienically while preventing bad odor in the accommodation box 210, and at the same time, the inconvenience of having to frequently clean the accommodation box 210 may be reduced.

In addition, the sheet providing unit 220 may include a sheet motor 229 that automatically rotates the roller shaft 225 (rotating in a rewinding direction), and in accordance with this, the controller 400 or the sub-housing 200 (or the accommodation box) may include a motor driving control module.

The motor driving control module may be linked with the urine analysis module 140 and drive the sheet motor 229 to withdraw the sheet 224 to the outside of the slit 226 while the urine analysis module 140 is analyzing the strip 10, and perform a function of determining whether to drive the sheet motor 229 based on a signal sensing whether the strip 10 is loaded on the bottom of the accommodation box from a load sensor that is additionally provided on the bottom of the accommodation box 210, that is, based on the presence of a load sensing signal. In other words, since there is no need to place a sheet on the bottom surface of the accommodation box 210 for each one of the strips 10, when it is recognized that the strip 10 is present in the accommodation box 210 via a load sensor, the sheet motor 229 is not driven, and otherwise the sheet motor 229 is driven, thereby providing a function of differentially controlling whether to drive the sheet motor 229.

By using the load sensor, the sheet motor 229, and the motor driving control module, the feature that hygiene may be ensured and also waste of the sheet 224 may be prevented by automatically controlling whether to withdraw the sheet 224 may be provided.

In addition, since the sheet 224 formed of a thin material such as vinyl may not be smoothly withdrawn to the space of the accommodation box via driving of the sheet motor 229 and may be rolled or folded, a sheet moving unit 230 may be further included.

The sheet moving unit 230 according to the present disclosure may move the sheet 224 by using, as a medium, a movable body 231 which is a slidably movable structure along a guide rail 233 in a forward and backward direction, and here, a clip that is foldable by user's manipulation may be formed on a surface of the movable body 231 facing the sheet, and the sheet 224 may be fixed by using the clip 232.

A rotator rotating along the guide rail 233 is formed on a lower surface (bottom surface) of the movable body 231, and furthermore, the rotator may be driven by an additional driving motor mounted inside the movable body 231, and may be driven by being linked with the sheet motor 229.

That is, by controlling rotation of the rotator in accordance with the number of revolutions of the sheet motor 229, by differentially controlling the number of revolutions of the driving motor of the movable body 231 based on a length of the sheet 224 withdrawn by the sheet motor 229, the feature that the sheet 224 may be moved to the front of the accommodation box 210 in accordance with the length of the sheet 224 as a result may be provided.

Furthermore, although not illustrated in the drawing, the sheet motor 229 may also be formed in an outer portion of the sheet housing 221 and one side of the sheet motor may be linked with the roller 223, and a pinion may be formed on the opposite side thereto to rotate the pinion, and this pinion may be linked with a rack that is additionally coupled to a lateral surface of the movable body 231 so that the rack is moved along the guide rail to thereby slidably move the movable body 231.

In this case, the feature that withdrawal of the sheet 224 and movement of the movable body 231 may be simultaneously performed using a single motor (the sheet motor) may be provided.

By using the sheet moving unit 230 as described above, when the sheet 224 formed of a thin material is withdrawn, the problem that the sheet is unnecessarily folded and thus does not easily cover the bottom surface of the accommodation box 210 may be properly prevented.

Figure 7:
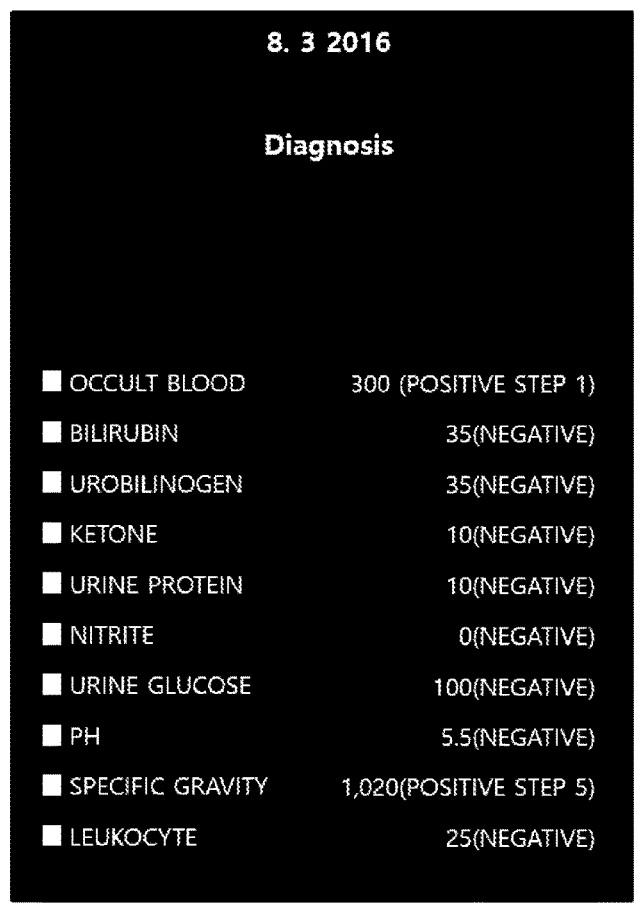
FIG. 7 is a conceptual diagram illustrating an example of a user interface (UI) of a mobile device linked with an analysis device according to the present disclosure.
Figure 8:
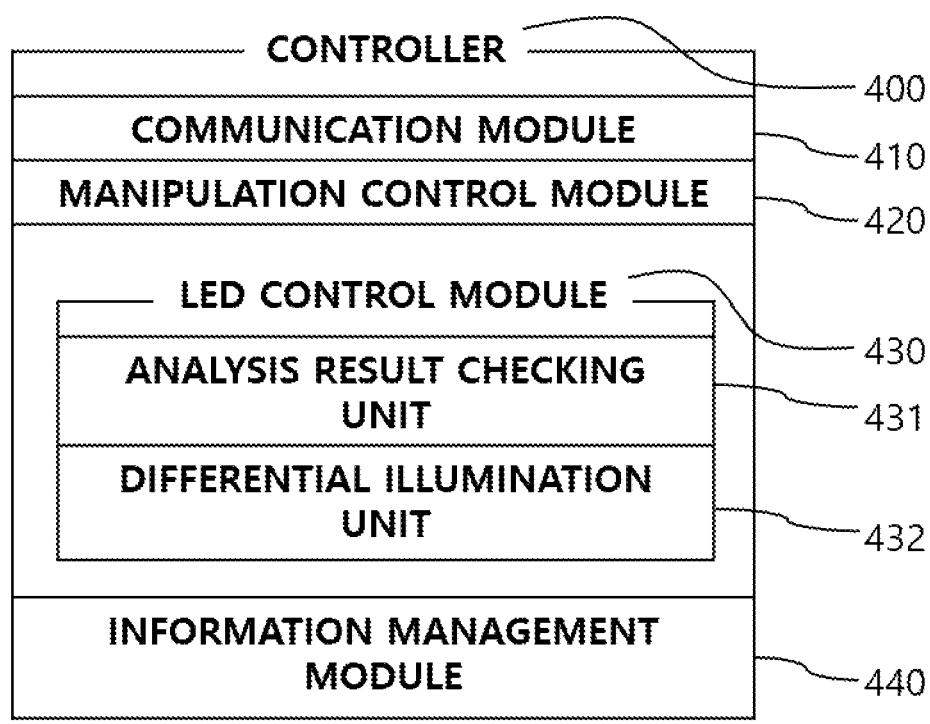
FIG. 8 is a block diagram illustrating a configuration of a controller according to the present disclosure.

FIG. 7 is a conceptual diagram illustrating an example of a user interface (UI) of a mobile device linked with an analysis device according to the present disclosure, and FIG. 8 is a block diagram illustrating a configuration of a controller according to the present disclosure.

As described above, the analysis device according to the present disclosure may be linked with a communication module (or a communicator) mounted in the analysis device of the present disclosure, via an application installed on a tablet PC or a mobile device to thereby allow not only manipulation control but also a convenient environment in which urine analysis information of each user may be recorded and stored.

The controller 400 according to the present disclosure performs a function of controlling/storing information for linkage with respect to an external electronic device such as a tablet PC or a mobile device, and may include a communication module 410 providing a communication function with respect to an external electronic device and a manipulation control module 420 that controls ON/OFF of the urine analysis device via manipulation of an application through communication by using the communication module 410 and performs tray driving control and also control driving of the sheet motor 229.

Moreover, an information management module 440 may be linked with an application installed on an external electronic device of the present disclosure and display, on the external electronic device, the urine analysis information of each user according to various categories and storage/display methods.

For example, as illustrated in FIG. 7, the information management module 440 may be linked with an application of an external electronic device to display a health condition of each user based on urine analysis information according to specific classification, and may also request a user a particular test based on the health condition or provide information about suspected disease. Moreover, by using an application, the information management module 440 may provide user registration/modification functions and also provide an additional function such as environment setting, provision of urine test history, etc.

Furthermore, the information management module 440 may provide various types of customized health guide information for each user, such as diet therapy (diet menus), kinesiotherapy, and other therapies, based on urine analysis information, and may even provide a function of searching for a nearby hospital and making reservations in case of a health problem.

In addition, the controller 400 according to the present disclosure may include a LED control module 430.

The LED module may also be mounted in a position other than on a urine analysis module, and may include not a monochromic LED but a LED package emitting light of a plurality of colors, and thus may emit light of particular colors such as red/yellow/green.

In conjunction with this, the LED control module 430 includes an analysis result checking unit 431 and a differential illumination unit 432.

The analysis result checking unit 431 performs a function of checking a health condition of a user based on urine analysis information analyzed using the urine analysis module 140, and the differential illumination unit 432 has a function of selecting a particular color of an LED module based on urine analysis information and emitting light in a manner as an indirect illumination, toward the support 300.

For example, when a result of urine analysis information of a user is determined to indicate a good health condition, the LED module may emit green light; when a result of urine analysis information is determined to indicate that a health problem is suspected, a yellow color may be displayed; and when a health risk is determined, a red color may be displayed. Here, the illumination may be provided such that light is emitted toward the support 300, and the support 300 may preferably be formed of a transparent material so that a delicate indirect illumination function may also be provided at the same time.

Accordingly, not only indirect illumination such as that of a mood lamp may be provided, but the feature of differentially displaying a health condition of a user based on illumination colors may also be provided.

While the structure and operation of the portable urine analysis device according to the present disclosure have been described above and illustrated in the drawings, the spirit of the present disclosure is not limited to the above description and drawings, and various changes and modifications may be made without departing from the technical spirit of the present disclosure.

The present disclosure may be mass-produced and conveniently used at homes, and is thus obviously industrially applicable.

What is claimed is:

1. A portable urine analysis device comprising:
a main housing comprising:
a tray comprising a strip loading portion on which a strip is loaded and a tray driving unit for driving the tray to be withdrawn out of or introduced into the main housing, wherein the strip loading portion is configured to be openable by an opening mechanism of the tray;
wherein the tray driving unit comprises a rack coupled to a side of the tray and a pinion that is connected to the rack and is rotated by driving of a motor;
a urine analysis module accommodated within the main housing for analyzing urine of the strip when the strip is introduced by the tray to a side of a urine analysis area to generate urine analysis information;
wherein the strip loading portion comprises a front loading portion facing a front side of the anaylsis device and a rear loading portion that is adjacent to the front loading portion, wherein the front loading portion and the rear loading portion are configured to be openabie, and
wherein the opening mechanism of the tray comprises a push frame extending from aside of the rear loading portion toward the front loading portion and a push spring mounted to the push frame to provide an elastic moving force to the push frame;
a sub-housing coupled under the main housing and comprising an accommodation box which is slidable with respect to the sub-housing; and
a support supporting the sub-housing;
wherein upon completion of urin analysis with the urine analysis module, the motor is driven to introduce the tray into a space at a back of the main housing such that the rear loading portion is brought into contact with an internal surface of the back of the main housing to compress the push spring, and as the elastic moving force of the push frame restores the front loading portion to its initial position, the strip loading portion is opened and the strip is dropped from the strip loading portion to the accommodation box and temporarily stored.

2. The portable urine analysis device of claim 1, wherein at least one of the main housing or the sub-housing comprises a LED module emitting light toward the support.

3. The portable urine analysis device of claim 1, wherein the main housing further comprises a base mounted on the internal surface of the back of the main housing and a push bar mounted on a rear side surface of the rear loading portion.

4. The portable urine analysis device of claim 1, further comprises a controller comprising a communication module performing a communication function, controlling the tray driving unit to drive the tray via manipulation of an application, and controlling the urine analysis module.

5. The portable urine analysis device of claim 4, wherein the controller further comprises an information management module that provides health guide information for a user based on the urine analysis information.

6. The portable urine analysis device of claim 2, wherein the LED module is formed of a LED package emitting light of at least two colors, and the urine analysis device comprises a LED control module that controls light emissions of the at least two colors of the LED package in different manner based on a result of the urine analysis information.

7. The portable urine analysis device of claim 1, wherein the accommodation box further comprises a sheet providing unit that is mounted in a sheet housing provided at one side at a back side of the accommodation box, the sheet providing unit comprising a roller that is rotatable via a roller shaft and winds a sheet, and a slit through which the roller is unwound to withdraw the sheet out of the slit such that the sheet covers a portion of a floor of the accommodation box.

8. The portable urine analysis device of claim 7, wherein the sheet providing unit further comprises a sheet motor that rotates the roper shaft to automatically withdraw the sheet.

9. The portable urine analysis device of claim 8, wherein the accommodation box further comprises a sheet moving unit comprising a movable body that is linked with the sheet motor along a guide rail formed on the floor of the accommodation box and is movable back and forth, and a dip that is mounted at a side of the movable body to couple and connect the sheet.

* * * * *